United States Patent

Wu et al.

[11] Patent Number: 5,814,729
[45] Date of Patent: Sep. 29, 1998

[54] SYSTEM FOR IN-SITU DELAMINATION DETECTION IN COMPOSITES

[75] Inventors: Shu-Yau Wu, Artesia; Donald L. Edberg, Irvine; Andrew S. Bicos, Huntington Beach, all of Calif.

[73] Assignee: McDonnell Douglas Corporation, Huntington Beach, Calif.

[21] Appl. No.: 709,932

[22] Filed: Sep. 9, 1996

[51] Int. Cl.[6] ................................................. G01N 29/00
[52] U.S. Cl. ............................ 73/588; 73/602; 73/768; 356/32; 356/35; 356/35.5
[58] Field of Search .......................... 73/596, 598, 599, 73/600, 579, 763, 768, 769, 775, 781, 799, 800, 801, 802, 582, 583, 588, 602; 364/506, 507, 508, 550; 250/227.14, 227.16, 227.17, 227.18; 356/32, 35, 35.5

[56] References Cited

U.S. PATENT DOCUMENTS

| | | | |
|---|---|---|---|
| 2,677,960 | 5/1954 | Moses | 73/588 |
| 3,038,329 | 6/1962 | Miller | 73/588 |
| 3,564,903 | 2/1971 | Woodmansee et al. | 73/588 |
| 3,597,962 | 8/1971 | Holtz | 73/588 |
| 3,623,358 | 11/1971 | Sugimoto | 73/588 |
| 3,762,496 | 10/1973 | Milberger et al. | 73/588 |
| 3,906,803 | 9/1975 | Pike | 73/588 |
| 3,937,065 | 2/1976 | Milberger et al. | 73/588 |
| 4,215,583 | 8/1980 | Botsco et al. | 73/582 |
| 4,231,259 | 11/1980 | Thiruvengadam et al. | 73/584 |
| 4,235,113 | 11/1980 | Carome | 73/655 |
| 4,494,410 | 1/1985 | Van Bochove et al. | 73/644 |
| 4,689,993 | 9/1987 | Slettemoen | 73/579 |
| 4,806,012 | 2/1989 | Meltz et al. | 356/32 |
| 4,836,030 | 6/1989 | Martin | 73/800 |
| 5,029,977 | 7/1991 | Wheeler et al. | 350/96.29 |
| 5,044,205 | 9/1991 | Wolff et al. | 73/800 |
| 5,118,931 | 6/1992 | Udd et al. | 250/227.16 |
| 5,182,449 | 1/1993 | Johnson et al. | 250/227.14 |
| 5,184,516 | 2/1993 | Blazic et al. | 73/799 |
| 5,195,046 | 3/1993 | Gerardi et al. | 364/506 |
| 5,305,507 | 4/1994 | Dvorsky et al. | 29/25.35 |
| 5,338,928 | 8/1994 | Jamieson et al. | 250/227.21 |
| 5,410,404 | 4/1995 | Kersey et al. | 356/345 |
| 5,513,913 | 5/1996 | Ball et al. | 374/120 |

*Primary Examiner*—Hezron E. Williams
*Assistant Examiner*—Richard A. Moller
*Attorney, Agent, or Firm*—Bell Seltzer Intellectual Property Group of Alston & Bird, LLP

[57] ABSTRACT

In a system for in-situ delamination detection in composites, the invention employs a system which evaluates the mechanical vibration response of composite material structures. The damping characteristics of the composite structure are extracted from the detected wave properties generated by imbedded piezoelectric ceramic actuators and received by imbedded high strain sensitive fiber optic sensors. Such a sensor system is simple to operate for real-time non-destructive strain and displacement monitoring and delamination detection, without the need to remove the tested surface from operation.

During the routine structural integrity monitoring operation, mechanical vibration pulses are launched into the composite from one actuator. The strain signal's propagation patterns are measured in real time by the fiber-optic sensors at different grating locations. Different travel times are computed dependent on the location of the receiving gratings.

Propagation of the waves through a delaminated area results in wave modal properties (damping characteristics) which show a difference from those propagating through the delamination-free area. Successive signals from different locations permit computation of the location of the delamination defect.

19 Claims, 7 Drawing Sheets

SYSTEM FOR IN-SITU DELAMINATION DETECTION IN COMPOSITES

BACKGROUND

1. Field of the Invention

The field of this invention relates to detection of defects in manufactured products. More specifically this invention relates to the detection of defects, such as delamination and delamination buckling in manufacturing of articles which comprise a series of plies of composite material attached to one another to form a complete structure.

2. Related Art

The detection of defects, such as delamination, and the investigation of delamination buckling in composites have become important topics of study in recent years. Delaminations may be formed from imperfections during the composite manufacturing processes, external loadings such as impact damage, cyclic fatigue, or environmental deterioration. The latter may occur in the operational life of the composite structure.

Delamination is one of the important failure modes in the laminated composite materials. It affects the strength and integrity of the composite structure and may cause structural degradation and eventual failure at a load less than the desired load. This is especially true under a compressive loading where the load-carrying plies lose the stabilizing structural support from the surrounding plies.

Numerous methods have been employed in the past to detect the delamination in the composite structures. These include visual inspection, videographic, x-ray, electron scanning, acoustic emission, ultrasound and MRI, etc. Most of the methods, however, involve extensive extravehicular measurements which require the temporary removal of the structure from service.

One method which not mentioned above is the vibration response method. This method has been used for non-destructive evaluation. It uses the frequency and phase signatures in the structural response functions together with system identification algorithms to identify changes in the monitored structures and to produce quantitative results. The method involves the use of vibration wave generating devices and wave detecting sensors such as accelerometers or strain gauges which are bonded to or embedded inside the monitored structure. The vibration waves are launched into the damaged structure from one location and the waves propagating through the damaged area are detected by sensors at other locations. Using a periodic system identifications the information carried by the detected waves such as the structural modal properties can be used to deduce the location and the extent of structural damage. However, the measured modal properties such as natural frequencies, mode shapes, dynamic response of the damaged, buckled or delaminated structure were based on or related to the system mass and stiffness parameters of the non-delaminated structure only. This use of measured modal properties to ascertain structural damage has not been very effective. For example, measurements on a 9.5 m rectangular truss where modal parameters were taken at the same time as one structural member of the truss was cut through its cross section causing a reduction of stiffness of as much as 40% in a single member had an almost indistinguishable effect on the system's first three vibration modes, as pointed out in D. L. Edberg, et al., "Theoretical and Experimental Studies of a Truss Incorporating Active Members," Journal of Intelligent Material Systems and Structures, Vol. 3, No. 2, pp. 333–347, April 1992.

It has also been determined that the detection of a delamination, and determining the extent of damage in a composite laminate using the mass and stiffness parameters alone is very difficult unless the size of the delamination in the structure is quite large, more than 30–50% of the normalized structure size, as discussed in J. J. Tracy and G. C. Pardoen, "Effect of Delamination on the Natural Frequencies of Composite Laminates," Journal of Composite Materials, Vol. 23, pp. 1200–1215, December 1989. In order to be able to detect a delamination more easily, therefore, a structural parameter other than the mass and stiffness may be employed.

The use of damping has been considered to be more sensitive for the detection of delaminations. Damping measurements in unidirectional composite beams have shown that longitudinal cracking is accompanied by a substantial change in the sample's damping. See D. L. Edberg, "Material Damping of Simple Structures in a Simulated Space Environment," Journal of Spacecraft and Rockets, Vol. 23, No. 3, pp. 288–296, May–June 1986.

While several means of determining changes to a structure using changes in wave propagation on the surface of a structure have appeared in a recent article by L. Berardinis, ie. "Touch and Go," Machine Design, Apr. 9, 1993, most of the strain sensors utilized in this approach are not very sensitive to measure changes in the damping characteristics. Therefore the crucial information in the damping characteristics is either not detected or is swamped by surrounding noise. This is one of the reasons why damping characteristics have not been implemented or been successful for delamination detention in composites, heretofore. The instant invention utilizes other sensitive strain-detecting sensors to resolve these problems.

The present invention describes a unique method and apparatus of detecting delaminations in composites using the vibration response method and apparatus for non-destructive evaluation, which may be used for detection of delaminations for structural integrity monitoring and damage assessment in composite structures for spacecraft, military and commercial aircraft, land vehicles, submarines, industrial hardware and equipment such as used for off-shore platforms and any other structures which employ composite materials.

BRIEF DESCRIPTION OF THE INVENTION.

It has been demonstrated in experimental work on truss and composite beam structures that a delamination can induce a substantial change in the damping characteristics.

The present invention specification describes a new method and apparatus for in-situ delamination detection in composites, unique from the previous methods mentioned earlier. The disclosed invention employs a method and apparatus which evaluates the mechanical vibration response of composite material structures. It is based on the analysis of information of the damping characteristics of the composite structure as extracted from the detected wave properties. The stress waves produced by the instant invention are launched from piezoelectric ceramic actuators embedded in known selected locations in the composite material and detected by high strain sensitive fiber-optic sensors also imbedded in the composite material at known locations and preferably on the surface thereof. Both the piezoelectric ceramic actuators and high strain sensitive fiber-optic sensors may be embedded in the composite material on manufacture. The fiber-optic sensors are very strain sensitive and simple to operate for a real time non-destructive strain and displacement monitoring and delamination detection.

The piezoelectric ceramic actuator patches may be embedded in the laminate structure near a series of fiber-optic sensors having gratings also embedded in the structure. During the routine structural integrity monitoring operation, mechanical vibration pulses are launched into the composite from one actuator. The strain signal, and propagation pattern are measured in real time by the fiber-optic sensors at different grating locations. Different propagation times are dependent on the distance between the receiving gratings and the actuator, the magnitude of the attenuation of such signals in an undamaged structure is dependent on propagation distance as determined for each grating. The waves detected by a grating will carry information regarding the damping characteristics of the structure through which the waves have propagated from the actuator location to the grating location.

If the waves have propagated through a delaminated area, the waves' spectral properties would show a difference from those propagating through the delamination-free area. A difference, indicating differing damping characteristics, gives an indication that structural delamination is in the path of the wave propagation. This monitoring process is repeated by launching waves from another actuator and the vibration responses monitored by the fiber-optic sensors again. Thus, by cross-monitoring with different actuators and gratings of fiber-optic sensors, and comparing the response patterns and the resulting damping characteristics between the damaged and the delamination-free structure, the system is able to locate through triangulation the delamination area and determine the extent of the damage.

It is an object of the instant invention to use changes in the structure's wave propagation resulting from damping to determine whether damage to a composite structure has occurred.

It is an object of the present invention to provide an apparatus which combines the use of piezoelectric ceramic actuators and high strain sensitivity fiber-optic sensors imbedded in the composite structure which permits defect detection through evaluation of damping characteristics in composites.

It is a further object of this invention to provide a more sensitive monitoring method and apparatus for non-destructive evaluation.

It is a further object of this invention to provide a more accurate technique for delamination detection, using changes in the structural damping computed from changes in the structure's wave propagation.

It is a further object of this invention to provide a detection system wherein stress waves are launched from actuators imbedded in the structure and the change in the magnitude of the structure's propagation wave are detected with high strain sensitive fiber-optic sensors also imbedded in the structure.

It is further object of this invention to provide a defect detection system which compares the wave attenuation properties from different sets of actuator-sensor combinations, and determines the location of the defect in the composite.

It is yet a further object of this invention to provide a simple non-destructive defect detection and evaluation method and apparatus without using sophisticated equipment such as x-ray, electron beam scanning, acoustic emission and magnetic resonance imaging or which involve extensive extravehicular measurements.

It is another object of this invention to provide a technique for detecting delaminations in structural areas which otherwise cannot be reached or unaccessible for detection by other known techniques.

It is another object of this invention to provide a low cost method and apparatus for routine monitoring and maintenance of composite structures without removing the structure from service.

BRIEF DESCRIPTION OF THE DRAWINGS

FIG. 5b is a continuation of 5a.

PREFERRED EMBODIMENT

Figure 1:
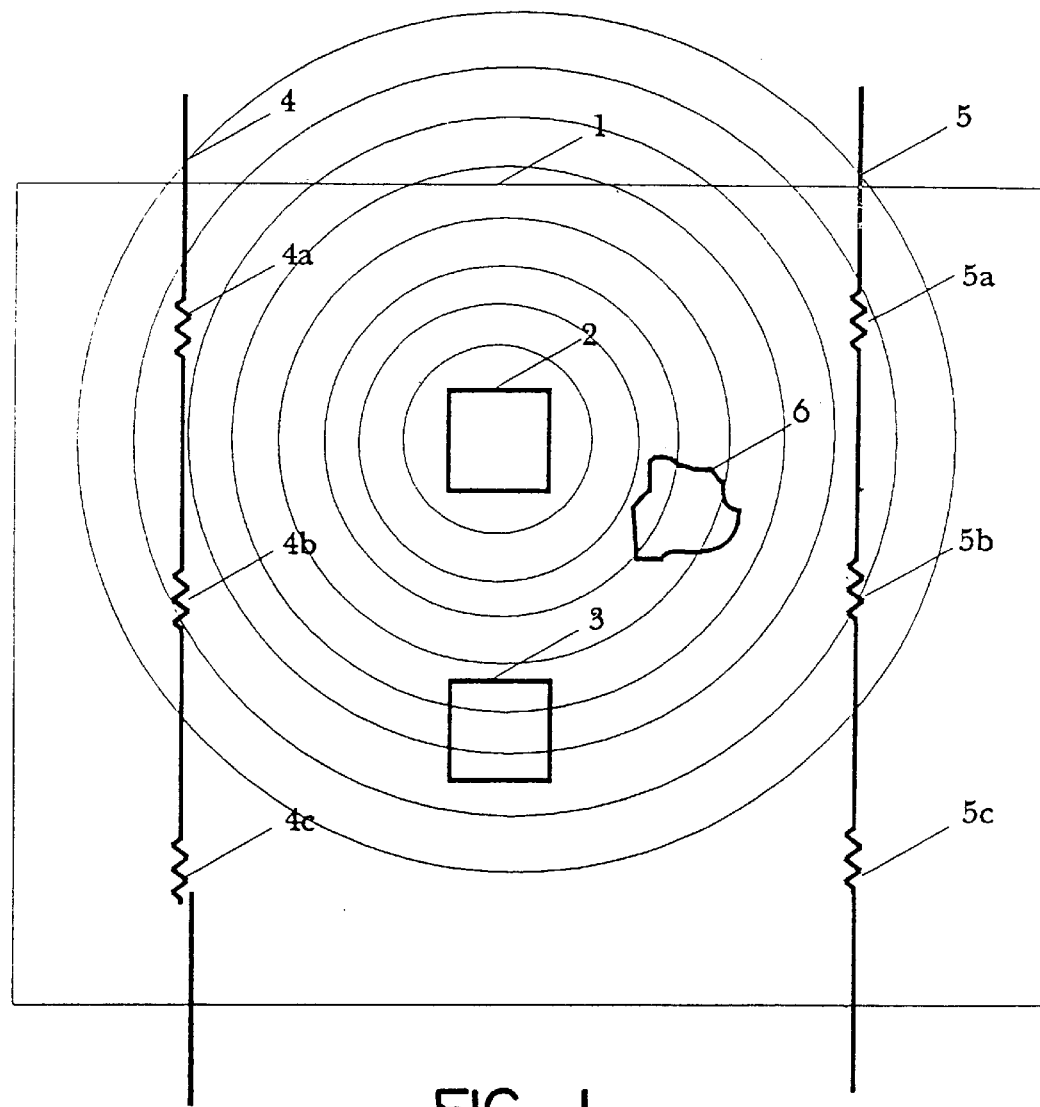
FIG. 1 shows a flat composite structure with piezoelectric ceramic actuator patches and fiber-optic sensor gratings imbedded.

With reference to FIG. 1, a flat composite structure 1 is shown with piezoelectric ceramic actuator patches 2, and 3 embedded near the center. Each of these actuators has a pair of electrodes (not shown) which are accessible from the outside of the composite structure 1 with wires (not shown) to permit electrical input to each actuator selectively. Alternatively, all actuator contacts may be reached at an access port for sequential access to each actuator. Fiber-optic sensors 4 and 5 each having three gratings 4a, 4b, 4c and 5a, 5b, and 5c respectively which are shown disposed on the left and right sides of the structure respectively. Each sensor should have at least one grating, ie. a spreading of the fiber strand into multiple strands or laser etched paths which occupy approximately twice the width of the fiber strand of the sensor. A delamination defect 6 is disposed between the piezoelectric ceramic actuators and at least one grating. During the routine structural integrity monitoring operation, mechanical vibration pulses are launched into the composite from one actuator 2 or 3 although more may be employed. The strain signal and propagation pattern are measured in real time by the fiber-optic sensors at different grating locations. This measurement is seen as a change in signal amplitude and damping factor in the transfer function through the optical fiber from the optical sensor. The waves detected by a grating will carry information related to the damping characteristics of the structure through which the waves have propagated from the actuator location to the grating location.

If the waves have propagated through a delaminated area, the wave spectral properties (damping or amplitude characteristics) would show a difference from those propagating through delamination-free area in the form of a degradation or attenuation of signal. This gives an indication that structural delamination 6 is present in the path of the wave propagation between the actuator 2, for example, and the sensor gratings 5a, 5b or 5c. This monitoring process is repeated by launching waves from another actuator 3, for example, and the vibration responses monitored by the fiber-optic sensors 4 or 5 again. By cross-monitoring with different actuators and different frequency tuned sensor gratings of fiber-optic sensors 4 and 5, and comparing the response patterns and thus the damping characteristics between the damaged and the delamination-free structure, the system is able to determine the location of the delamination area with reasonable accuracy and in some cases determine the extent of the damage.

The sensor signal is caused by deformation of the fiber optic sensor walls due to mechanical stresses which changes propagation characteristics within the fiber. The mechanical strain may then be detected by demodulating the phase shift as is currently known in the art.

Figure 2:
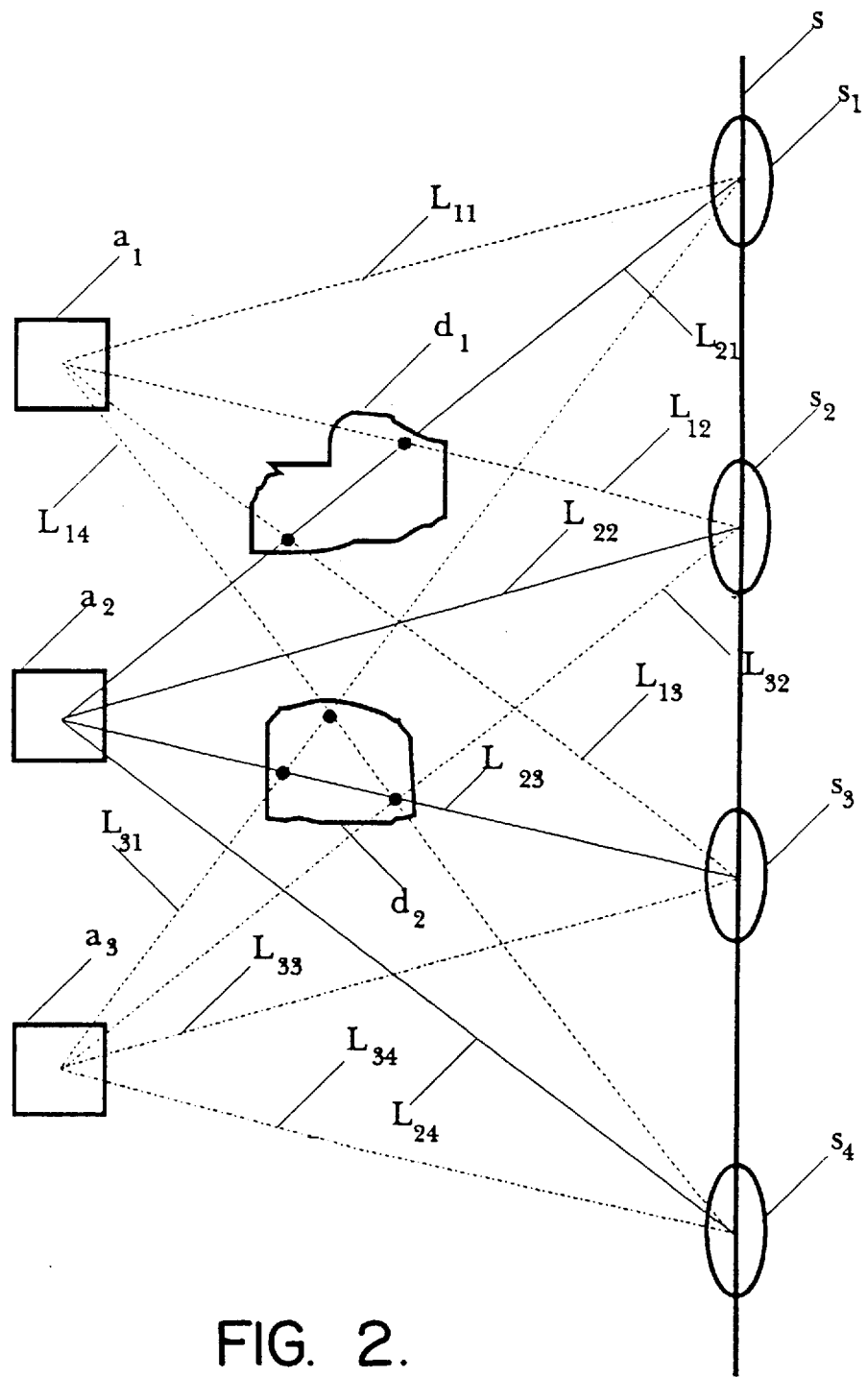
FIG. 2 is a diagrammic view of actuators' propagation paths to sensors.
Figure 3:
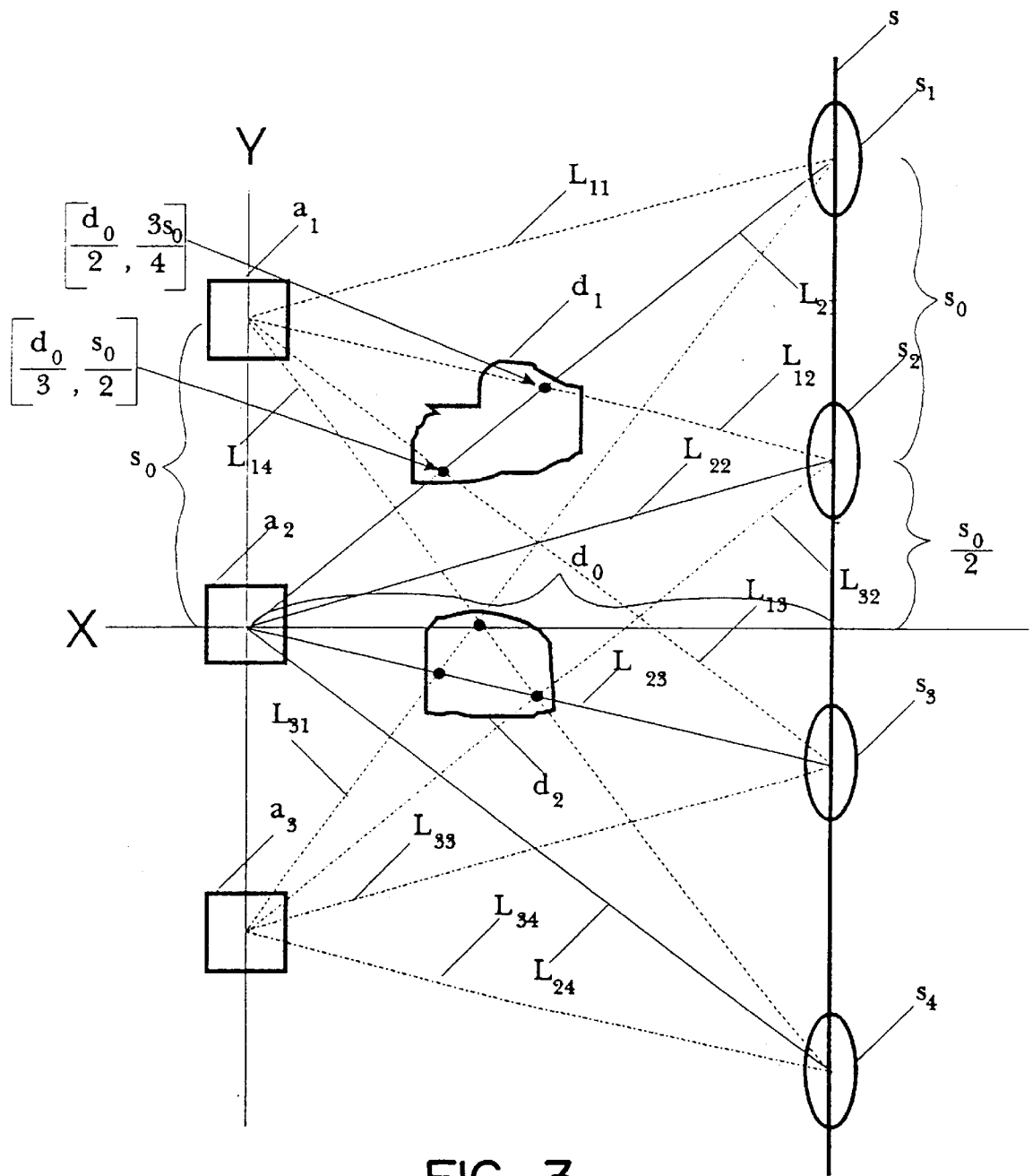
FIG. 3 is a diagrammic view superimposing an X, Y coordinate system on said actuator sensor system.

FIG. 2 shows the most direct line of propagation for actuators $a_1$, $a_2$ and $a_3$ to the respective sensors $s_1$, $s_2$, $s_3$ and $s_4$. Defects $d_1$ and $d_2$ are disposed between the actuators and the sensors. As can be seen there are a number of intersections between the respective paths from the actuators to the sensors within the defect regions. As some paths are defect-free such as L11, L22 and L24, both intersecting paths and delamination free paths are used in the defining defect location. FIG. 3 illustrates the manner in which the intersecting paths may be calculated by superimposing X, Y coordinates on the actuator sensor structure.

When a reduction in amplitude is detected which is different than that expected for normal attenuation in the lamination, the specific sensor is identified as described before and the propagation line between the sensor and the actuator is represented by a series of straight lines as shown in FIGS. 2 and 3.

The formula for a line is in the general form of Y=mX+b, where m is the slope of the line and b is the offset from the reference Y axis.

With reference to FIG. 3, the formula is rewritten as follows:

Y=mX+c where c=the offset on Y axis from the origin

FIG. 3 shows actuators $a_1$, $a_2$ and $a_3$ opposite sensor gratings $s_1$, $s_2$, $s_3$ and $s_4$ on an optical fiber strand S. The actuators lie on a line (although the actuators are not directly connected) which is disposed parallel to the sensor strand S and spaced apart at distance $d_o$ as shown in the figure. Each of the sensor gratings is spaced equal distance along the sensor line at distance $s_o$. For this example, sensors $s_2$ and $s_3$ are disposed equal distance from the line X through the center of $a_2$. Disposed between the sensors and the actuators are two defects, $d_1$ and $d_2$. Focusing on the actuator lines from $a_1$ to $s_1$, $s_2$, $s_3$ and $s_4$, which are identified respectively as $L_{11}$, $L_{12}$, $L_{13}$ and $L_{14}$ and on the lines from actuator $a_2$ to $s_1$, $s_2$, $s_3$, and $s_4$ identified as $L_{21}$, $L_{22}$, $L_{23}$ and $L_{24}$: When actuator $a_1$ is activated, sensor $s_1$ receives an unattenuated signal. Sensor $s_2$ will receive an attenuated signal. Sensor $s_3$ will receive an attenuated signal and Sensor $s_4$ will receive an attenuated signal. It should be noted that $s_4$ receives an attenuated signal due to a different defect, defect $d_2$. The second defect is included only for the purposes of demonstrating the manner in which different defects can be discriminated.

FIG. 3 shows a defect $d_1$ which is intersected by signals from $a_1$ which are detected by sensors $s_2$ and $s_3$ respectively. The detection of $a_1$ signals at such sensors defines propagation lines $L_{12}$ and $L_{13}$ as shown. The same defect is also intersected by signals from $a_2$ which is detected by sensor $s_1$ only. The detection of $a_2$ signals defines a propagation line $L_{21}$. $s_2$ also detects such signal on a defect free path $L_{22}$. The intersection of Line $L_{12}$ and Line $L_{21}$ determines the site of the detected delamination at such intersection. The intersection of Line $L_{13}$ and Line $L_{21}$ also determines another site of a detected delamination at their point of intersection. The general formula for such intersections is determined as follows:

For line $L_{12}$:

$$m = -\left(\frac{0.5 S_o}{d_o}\right), c = S_o$$

$$y = -\frac{0.5 S_o}{d_o} X + S_o$$

or
For line $L_{21}$ $$m = \frac{1.5 S_o}{d_o}, c = 0$$

or $$y = \left(\frac{1.5 S_o}{d_o}\right) X$$

The calculation for the point of intersection of these lines is as follows:
Setting Y=Y yields:

$$\left(\frac{-0.5 S_o}{d_o}\right) X + S_o = \frac{1.5 S_o}{d_o} X$$

Solving for X yields:

$$X = \left(\frac{1}{2}\right) d_o$$

Solving for Y yields:

$$Y = \frac{3}{4} S_o$$

Thus, the sensors have detected a delamination at point $d_o/2, 3s_o/4$, where the actuator $a_2$ is the reference point.

Similarly, solving the equations for line $L_{13}$ and $L_{21}$ yields
For line $L_{13}$ $$m = -\frac{1.5 S_o}{d_o}, c = S_o$$

$$Y = -\left(\frac{1.5 S_o}{d_o}\right) X + S_o$$

or
For line $L_{21}$ $$m = \frac{1.5 S_o}{d_o}, c = 0$$

or $$Y = \left(\frac{1.5 S_o}{d_o}\right) X$$

The calculation for the point of intersection of these lines is as follows:
Setting Y=Y yields:

$$-\frac{1.5 S_o}{d_o} X + S_o = \frac{1.5 S_o}{d_o} X$$

Solving for X yields:

$$X = \frac{d_0}{3}$$

Solving for Y yields:

$$Y = \frac{S_o}{2}$$

Thus, the sensors have detected delamination at points $(d_0/3, s_o/2)$ and $(d_0/2, 3s_o/4)$ where the actuator $a_2$ is the reference point. It can be appreciated that the mathematics operates regardless of where the origin is placed taking care to account for the appropriate offset from the origin, whatever it may be.

Each actuator sensor pair which detects the set attenuation deviation defines a line which permits the calculation of the intersection points of multiple lines of other actuator/sensor pairs. The patterns of intersection points for multiple lines thus defines the delamination area by a series of points, as shown on FIG. 4. The lines which do not intersect such as $L_{22}$ and $L_{11}$ on FIG. 3 indicate delamination-free paths. The existence of delamination-free lines and line segments is used to isolate defect intersection locations into discrete defect regions. In FIG. 3, the sensors $s_1$ and $s_2$ will register no attenuation other than that experienced due to distance over the propagation path and thus define a line which passes through the lamination without encountering a delamination region. Such lines intersect with various other lines and define intersection points which define nominal or undamaged areas and thus restrict the detected delamination intersection points to discrete delaminated areas or regions. In addition, there are delamination-free regions of other intersection lines which intersect the delamination-free lines shown as solid lines on FIG. 3. These are, for example, line $L_{14}$, which encounters no defects from the actuator to the intersection with $L_{22}$ and $L_{31}$, which after encountering the defect $d_2$ encounters no defect from the point of intersection with line $L_{22}$ to the actuator $s_1$. These line segments may also be calculated and plotted to discriminate and isolate the location of various defects. Such line segments are shown on FIG. 4 as dotted lines.

It is clear that the larger the number of actuators or sensors, the more accurate and discriminating the delamination detection becomes.

It should be noted that for illustration purposes, only four signal paths generated by each of the three actuators are shown which as detected by the four sensors. However, each actuator generates signals which travel over an infinite number of paths in every direction. As a given signal travels over a path to a remote sensor its signal may be significantly diminished and the benefit of calculating all possible signal paths is therefore a case of diminishing returns. As a practical matter the discrete sensor gratings are tuned spectrally over a limited discrete number of different frequencies and thus a practical limitation exists due to current technology limitations. Up to ten different sensor grating frequencies for example may be utilized on an optical fiber to avoid overlapping data signals for sensors at different locations which are equidistant from a given actuator, such as $s_1$ and $s_4$ in FIG. 3 which are equidistant from actuator $a_2$, and $s_1$ and $s_2$ which are equidistant from $a_1$. It is clear that where sensor gratings on the same optical fiber are equidistant from a given actuator that the detected phase shifts would overlap if each grating were tuned to the same frequency.

Again referring to FIG. 3 actuators, $a_1$, through $a_3$ each actuator would sequentially generate a signal, which is detected by the fiber optic gratings each grating $s_1$, through $S_4$ responds to such signal by a discrete phase shift in the optical signal traveling down the fiber. Since the signal travels at the speed of light the fiber transmission time can be ignored. The sensor detector at the end of fiber optic strand can demodulate the phase shift in each of the different frequency sensors thus identifying (detecting) the presence or absence of a delamination between the actuator generating the signal somewhere along the path to the specific sensor.

Figure 4:
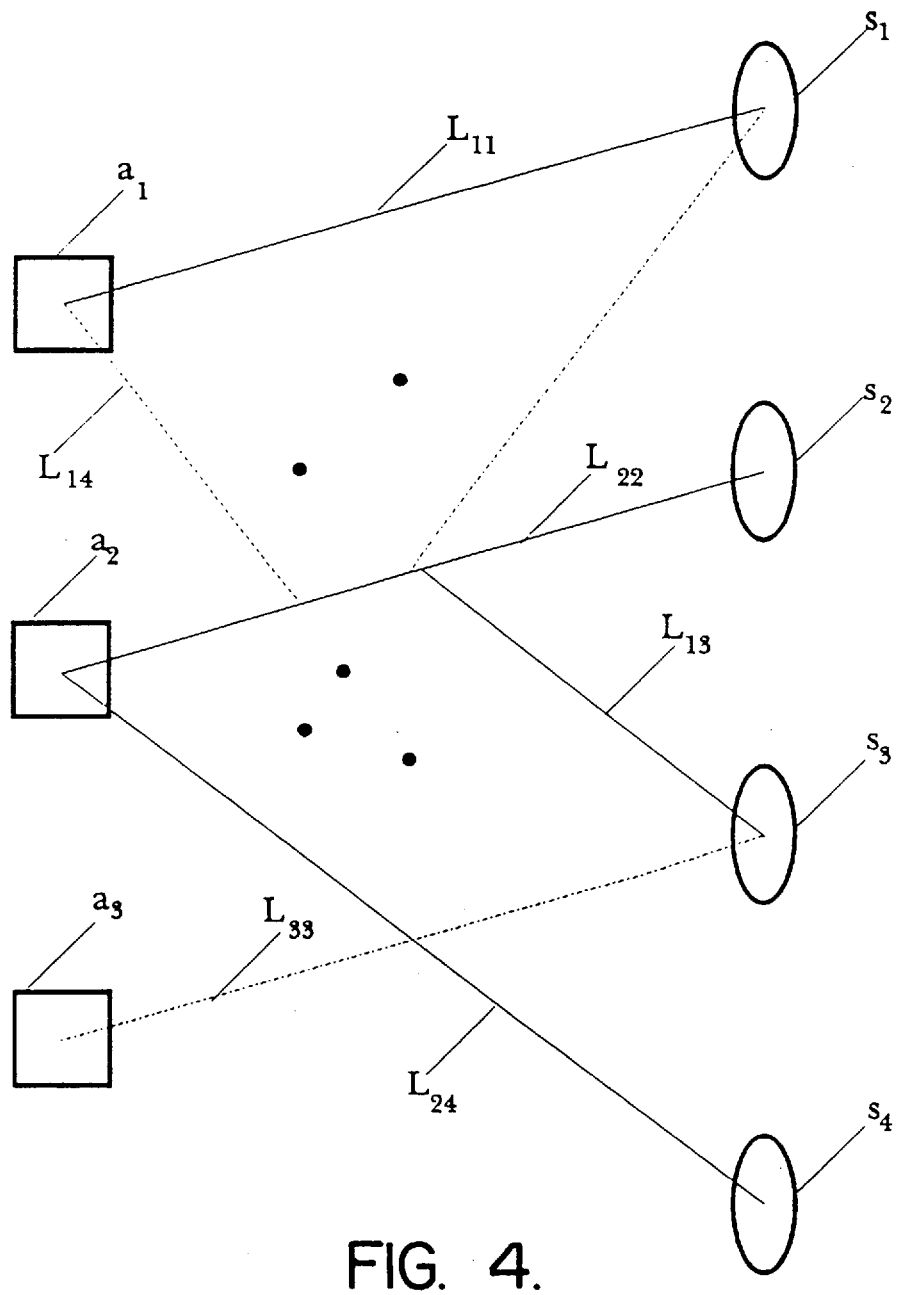
FIG. 4 is a diagrammic view of detected defect locations and lines representing defect free paths.

On detecting a delamination signal a computer or controller may compute the intersection paths of a selected number of actuator sensor paths adjacent to the detected region based on the prior disclosed formula until a clear path is found on either side of the detected delamination region. The computation of intersection paths continues throughout the laminated structure until all delamination detected intersections have been evaluated. FIG. 4 illustrates the results of such calculations showing the number of clear path lines (solid lines), or line segments (dashed lines) of intersect lines representing a clear paths between the actuator and another delamination-free solid line or sensor grating, and then a number of points disposed between such areas indicating the presence of defect line intersections.

The computations commence at the first detected delamination region. If the delamination is found at a boundary layer i.e., the first actuator tested, it is possible that no free path can be found on both sides of the delamination detected. In such a case the delamination evaluation will not determine a delamination free area on both sides of the delamination area, however, the manner of evaluation will proceed as before and the delamination defect will be bounded on only one side with a delamination free line.

Figure 5A:
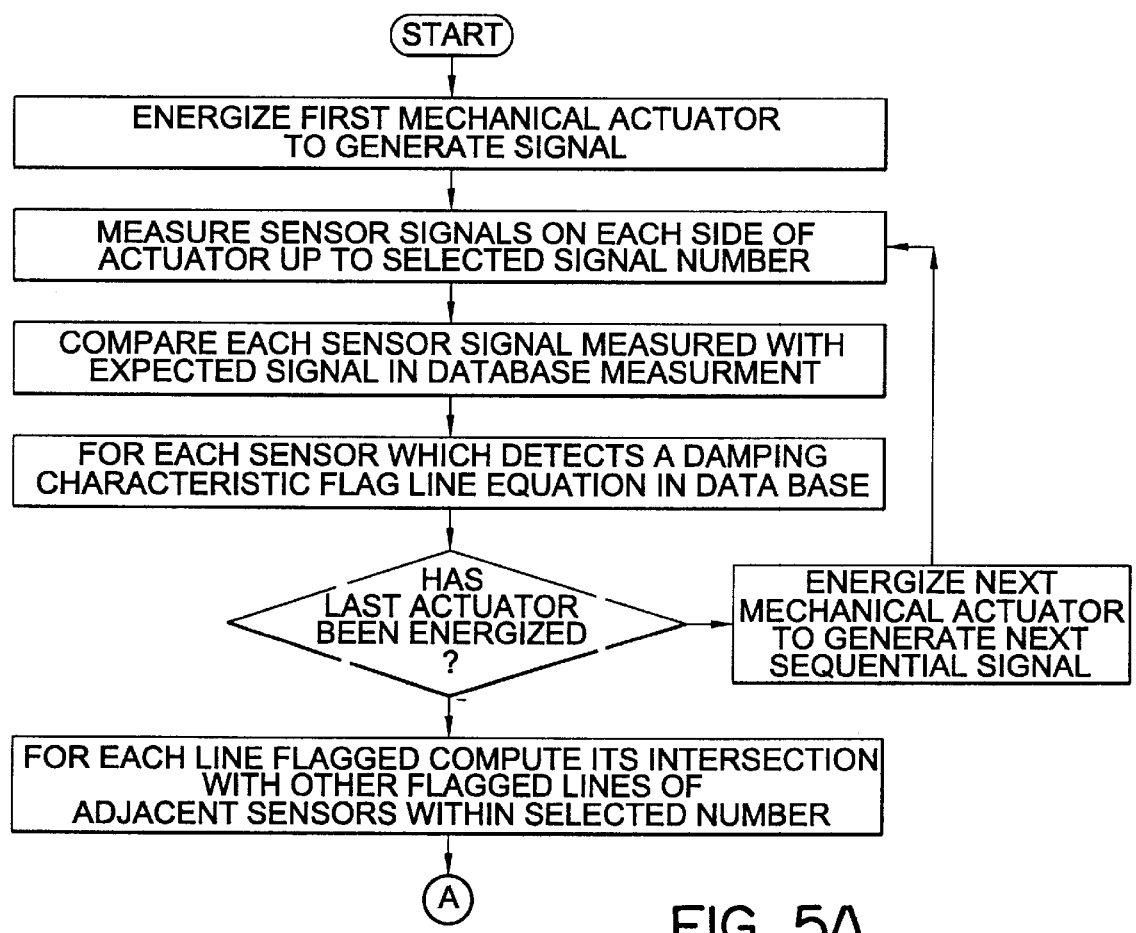
FIG. 5a is a flow chart of the detection system steps.

FIG. 5a shows a flow chart of the delamination detection system method which may be implemented on a general or special purpose computer, which computes a pattern of delamination intersection point location for the part being tested and stores such point locations representing each intersection in memory. A report can be generated which specifically locates each of the delamination intersections on a part, grouping such delamination intersections to groups within the area or areas bounded by delamination free lines. Alternatively, the data stored and both dashed line segments and solid lines may be displayed on a display screen or plotted on a plotter.

The system obtains data signals for the nearest five sensors on the side adjacent to each actuator although any particular number may be used. Each actuator commencing with the first is energized in a different time window in order to determine the origin of the signal and to compute the propagation paths. Upon the detection of a delamination on any line, the intersection calculations are conducted on the five sensors on each side of the detected delamination line and the data stored. When each of the group of the first ten actuators has been energized, the next group of ten actuators begins the sequential generation of signals and the system obtains another set of data signals. The data from the last set of ten actuators is retained and used for the five sensors on the side of any detected delamination in the subsequent group. Thus, the area of inquiry is incremented through the material being evaluated by five actuator sensor pairs until all intersections adjacent to delamination detections have been calculated. All intersection points are stored in memory and all delamination-free lines and delamination-free line segments are stored in memory including their start and end points.

Figure 6:
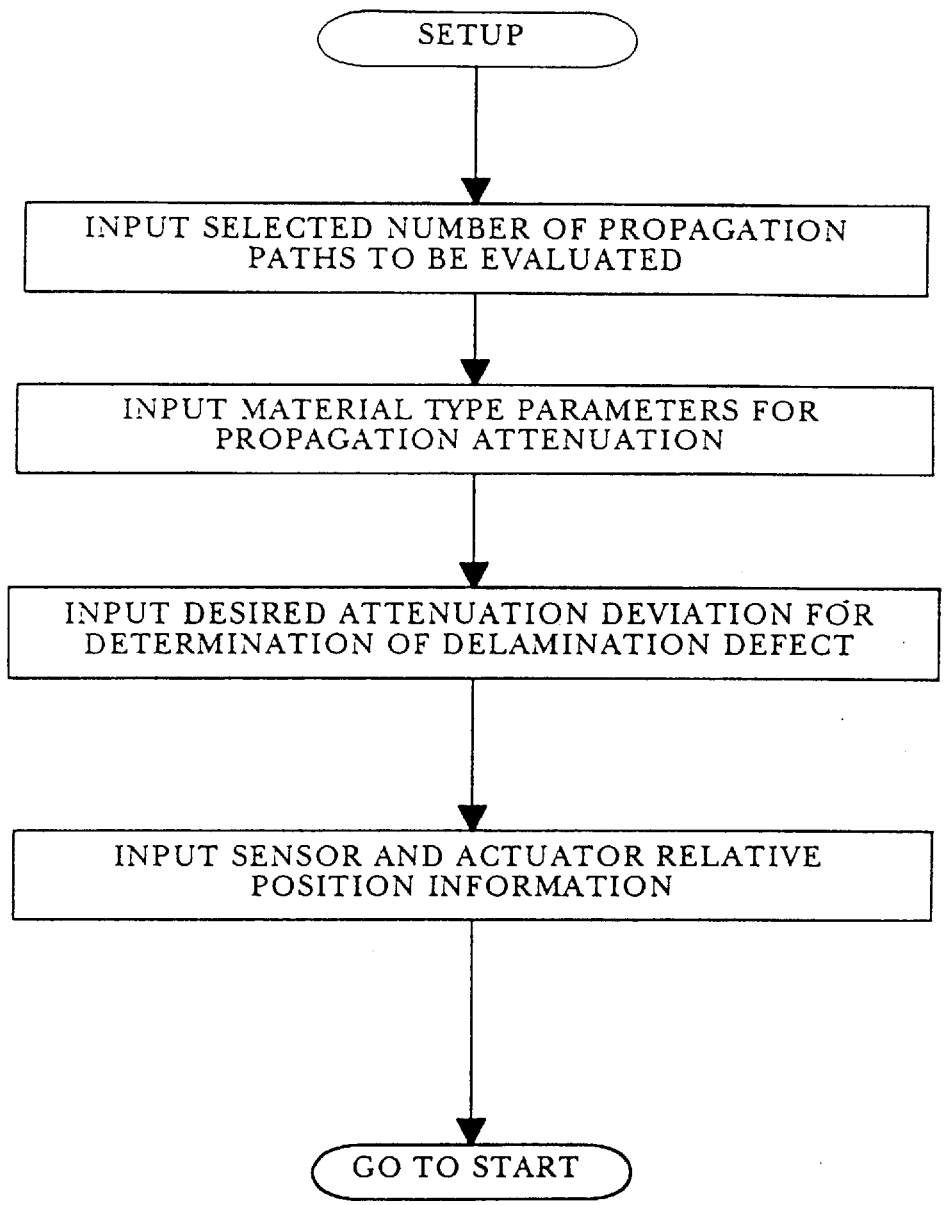
FIG. 6 is a flow chart of setup steps for the particular laminate.

The system also stores all of the data so acquired for future reference in a database related to specific parts such as a specific wing on a specific aircraft. In fact, it is recommended that data on a part be taken when placed into service which is initially without any delamination defects and recorded for future comparison and for more precise calibration of the propagation characteristics of the given part between all sensors. Initial empirical data is also stored regarding the propagation characteristics of any given part as initial conditions as shown in FIG. 6. In this way, the initial test can determine delamination in a new part due to defects in manufacture when first placed in service or during assembly, so that repairs can be made prior to installation.

Figure 5B:
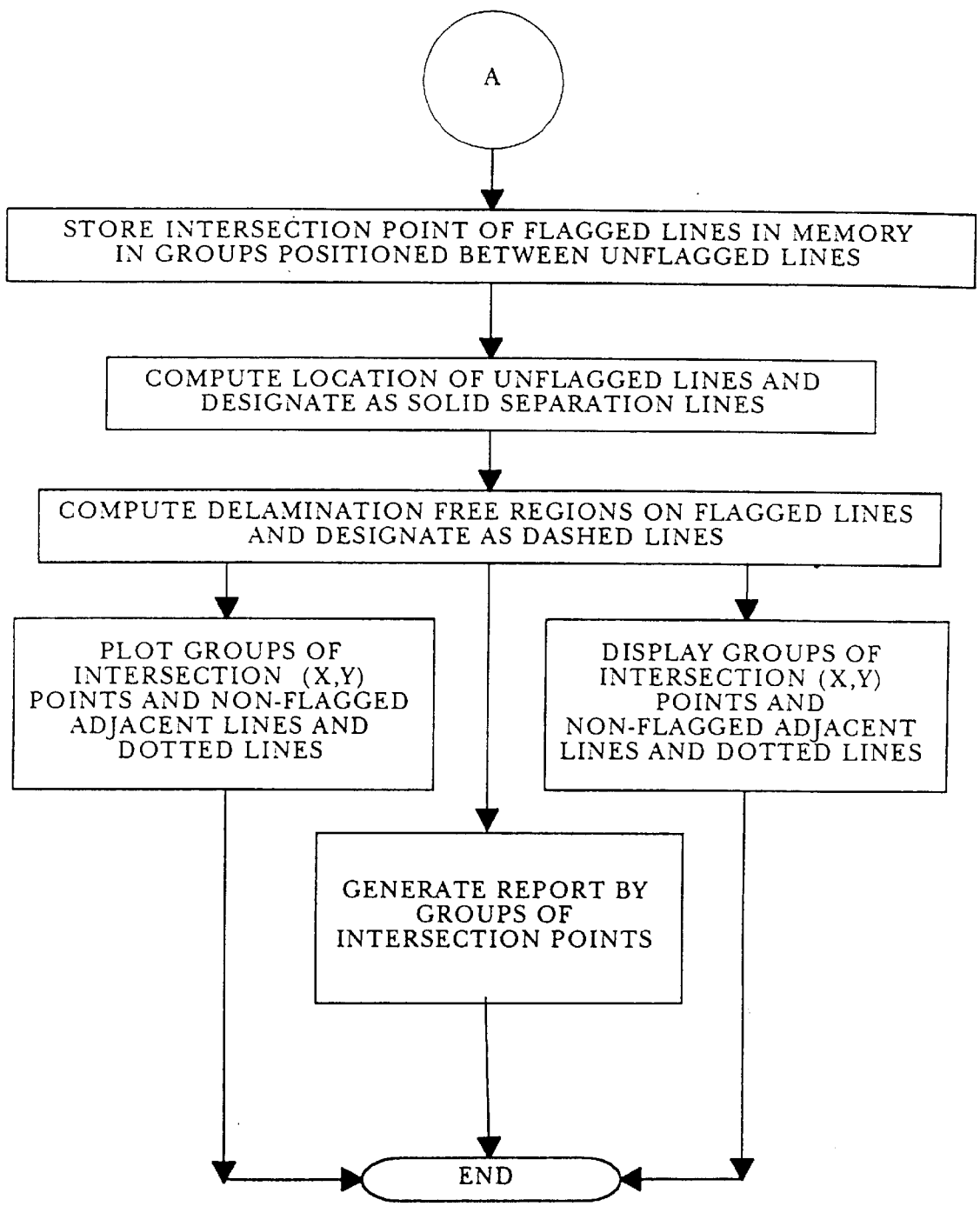

The evaluation steps shown in FIG. 5a commence at step 100 which energizes the first mechanical actuator to generate a signal for step 101. Each of the sensor signals is demodulated for a selected number of sensors on each side of the energized actuator, such as 5, for example, for a total of 10 sensor signals, step 102. Each demodulated sensor signal is measured and compared against the signal in the database, which represents the delamination-free area, step 103. Each actuator/sensor pair which detects a damping factor greater than that desired is flagged in the database to indicate that a defect has been detected, step 104. The computer system evaluates whether the last mechanical actuator has been energized and, if not, it proceeds to energize the next mechanical actuator in sequence to generate another signal, step. 107. Measurements commence anew in step 102. If the last actuator in the part has been energized, the computer then computes the intersection of each line flagged with each other line flagged in the group of ten sensors, the five on either side of said actuator. In the case of FIG. 3 for example, there are two sensors above actuator $a_2$ and two sensors below actuator $a_2$ as shown in the figure. The process continues as shown in FIG. 5b where in step 108 each of the intersection points is stored in memory in groups identified as being between unflagged lines, that is delamination-free lines. Delamination-free lines are computed in two ways, as shown in FIG. 4. First, the delamination-free paths from the actuator direct to the sensors in question are computed and are shown on FIG. 4 as solid lines. Then the dotted line, delamination-free segments of intersecting lines are computed to illustrate the delamination-free portion of such lines between the actuator and the most adjacent solid line and from the solid line to the adjacent sensor or even between solid lines, as shown in step 110. The beginning points of such dotted lines would be their respective actuator and the end point which intersects with a solid delamination-free line, that portion of the line which commences from a solid delamination-free line and ends on its respective sensor or that portion of the delamination-free line which commences and ends on solid delamination-free lines. Once the solid lines' and dotted lines' intersection points are determined, they may be displayed on a CRT as the groups of the intersection X Y points and the solid and dotted lines are plotted on a plotter as groups of X Y points and solid and dotted lines. Alternatively, they may also be set forth in a report which is generated to show the intersection points in the groups using their X and Y coordinates. Each group designating delamination intersection points bounded by solid and dotted lines are segregated as a delamination group representing a single delamination region. These are set forth in steps 111, 112, and 113 and the test process in step 114. FIG. 6 shows the initialization setup, step 200, which permits the input of the selected number of propagation paths to be evaluated, that is the five sensors above or below the actuator, which occurs in step 201. Step 202 permits the input of the material type or the designation of the specific parameters for propagation attenuation against which the detected signals will be compared. Step 203 permits an input for a desired attenuation deviation for determination of delamination. Some reasonable percentage of deviation should first be required before signaling that a defect has been located to avoid all intersections being computed for minor point delaminations within acceptable limits. In step 204, the sensor and actuator relative position information is input for the particular structure being tested, those figures are determined on manufacturing of the product. After the input of such information, the actual testing may commence and the setup then goes to the start setting point 100.

While the invention has been described in terms of a two dimensional plane, it is clear that the actuators and sensors will be imbedded in a three dimensional structure. Since this third dimension is small compared with the dimensions of the overall structure, it can be ignored. However, more sophisticated detection systems may incorporate calculations relative to the depth of the planar structure.

In addition, while no planar orientation of the detector relative to the actuators has been otherwise disclosed, it is preferred that the plane of the detector grating be disposed generally parallel to the plane of the structure for maximum signal interception. However, any orientation of such detector grating is operable.

Having thus described the invention, what is claimed is:

1. A sensor system for detecting a defect in laminated composite structures comprising:

at least one mechanical actuator, in operable contact with said laminated composite and adapted for generation of a vibration wave that propagates as a vibration signal along at least one propagation line extending through said laminated composite structure;

at least two delamination sensors, in operable contact with said composite structure, for sensing vibration signals generated by said actuator and propagating along propagation lines defined between said actuator and respective ones of said delamination sensors; and delamination detection means in operable communication with said delamination sensors for evaluation of said sensed vibration signals that have propagated along propagation lines defined between the actuator and said delamination sensors, wherein said delamination detection means comprises:

means for analyzing the vibration signals propagating along the propagation lines and detected by said respective delamination sensors to determine whether the propagation lines extend through a delamination region in said laminated composite structure;

means for categorizing each of said propagation lines wherein said categorizing step categorizes propagation lines which extend through a delamination region as delamination lines and categorizes propagation lines which do not extend through delamination regions as delamination-free lines; and means for determining the presence of a delamination region, the location of said delamination region, and boundaries of said delamination region based on the relative positions of said delamination lines and said delamination-free lines.

2. A sensor system as described in claim 1 wherein the mechanical actuator is a piezoelectric actuator.

3. A sensor system as described in claim 1 wherein said mechanical actuator is imbedded in the laminated composite structure.

4. A sensor system as described in claim 1 wherein said analyzing means comprises means for analyzing the vibration signals propagating along the propagation lines to determine whether said vibration signals are dampened such that the amplitude of the vibration signals exceeds a predetermined attenuation limit indicating that said propagation lines extend through a delamination region.

5. A sensor system as described in claim 1 wherein said delamination sensors for sensing vibration signals generated by said actuator are embedded in the laminated composite structure.

6. A sensor system as described in claim 1 wherein said determining means determines the location of said delamination regions by excluding regions in which delamination-free lines extend therethrough.

7. A sensor system as described in claim 1 wherein said determining means determines the boundaries of said delamination region by designating delamination-free lines which are adjacent to delamination lines as boundaries for said delamination region.

8. A sensor system as described in claim 1 wherein said at least one mechanical actuator comprises a plurality of mechanical actuators, wherein said at least two delamination sensors comprise a plurality of delamination sensors, and wherein said means for determining the boundaries of the delamination region constructs a boundary surrounding the delamination region that includes segments of at least three delamination-free lines which are adjacent to at least a portion of a delamination line.

9. A sensor system as described in claim 1 wherein said delamination sensors comprise a fiber optic strand having at least two fiber optic gratings spaced along the length of said fiber optic strand, and wherein said fiber optic gratings sense said vibration signals generated by said mechanical actuator.

10. A sensor system as described in claim 9 wherein said fiber optic gratings are tuned to different frequency ranges and said fiber optic strand provides a modulated sensing signal output containing the sensed signals sensed by each of the fiber optic gratings.

11. A sensor system as described in claim 10 wherein said sensor system further comprises demodulating means connected to said fiber optic strand, and wherein said demodulating means demodulates the modulated sensing signal output by said fiber optic strand into individual sensing signals representing the vibration signals sensed by each of said fiber optic gratings.

12. A sensor system for detecting a defect in laminated composite structures comprising:
at least two mechanical actuators in operable contact with said laminated composite, each mechanical actuator adapted for generation of a vibration wave that propagates as a vibration signal along at least one propagation line extending through said laminated composite structure;
at least one delamination sensor, in operable contact with said composite structure, for sensing said vibration signals generated by each of said actuators and propagating along propagation lines defined between said actuators and said delamination sensor; and
delamination detection means in operable communication with said delamination sensor for evaluation of said sensed vibration signals that have propagated along propagation lines defined between the actuators and said delamination sensor, wherein said delamination detection means comprises:
means for analyzing the vibration signals propagating along the propagation lines and detected by said delamination sensor to determine whether the propagation lines extend through a delamination region in said laminated composite structure;
means for categorizing each of said propagation lines wherein said categorizing step categorizes propagation lines which extend through a delamination region as delamination lines and categorizes propagation lines which do not extend through delamination regions as delamination-free lines; and
means for determining the presence of a delamination region, the location of said delamination region, and boundaries of said delamination region based on the relative positions of said delamination lines and said delamination-free lines.

13. A sensor system as described in claim 12 wherein said actuators generate vibration waves sequentially such that only one vibration wave from only one actuator is propagating as a vibration signal through said laminated composite at a time.

14. A sensor system as described in claim 12 wherein said determining means determines the location of said delamination regions by excluding regions of the laminated composite structure through which delamination-free lines extend.

15. A sensor system as described in claim 12 wherein said determining means determines the boundaries of said delamination region by designating delamination-free lines which are adjacent to delamination lines as boundaries for said delamination region.

16. A sensor system as described in claim 12 wherein said at least two mechanical actuator comprise a plurality of mechanical actuators, wherein said at least one delamination sensor comprises a plurality of delamination sensors, and wherein said means for determining the boundaries of the delamination region constructs a boundary surrounding the delamination region that includes segments of at least three delamination-free lines which are adjacent to at least a portion of a delamination line.

17. A method for detecting defects in laminated composite structures comprising the steps of:
sequentially generating vibration waves at a plurality of predetermined generating locations spaced along said laminated composite structure, wherein said generating step generates vibration waves that propagate as vibration signals along each of a plurality of propagation lines extending through said laminated composite structure;
sensing, at a plurality of sensing locations spaced along said composite structure, vibration signals generated in said generating step that have propagated along propagation lines defined between said plurality of generating locations and said respective plurality of sensing locations;
analyzing the vibration signals propagating along the propagation lines and sensed in said sensing step to determine whether the propagation lines extend through a delamination region in said laminated composite structure;
categorizing each of said propagation lines, wherein said categorizing step categorizes propagation lines which extend through a delamination region as delamination lines and categorizes propagation lines which do not extend through delamination regions as delamination-free lines; and
determining the presence of a delamination region, the location of said delamination region, and boundaries of said delamination region based on the relative positions of said delamination lines and said delamination-free lines.

18. A method as described in claim 17 wherein said determining step comprises the step of determining the location of said delamination regions by excluding regions of the laminated composite structure through which delamination-free lines extend.

19. A method as described in claim 18 wherein said determining step further comprises constructing a boundary surrounding the delamination region that includes segments of at least three delamination-free lines which are adjacent to at least a portion of a delamination line.

* * * * *